US00PP19018P2

(12) United States Plant Patent
Smith

(10) Patent No.: US PP19,018 P2
(45) Date of Patent: Jul. 15, 2008

(54) ***ASTER* PLANT NAMED 'YOPETER THE THIRD'**

(50) Latin Name: *Aster hybrida*
Varietal Denomination: Yopeter the Third

(75) Inventor: Mark A. Smith, Fort Myers, FL (US)

(73) Assignee: Yoder Brother's Inc., Barberton, OH (US)

( * ) Notice: Subject to any disclaimer, the term of this patent is extended or adjusted under 35 U.S.C. 154(b) by 0 days.

(21) Appl. No.: 11/705,877

(22) Filed: Feb. 14, 2007

(51) Int. Cl.
*A01H 5/00* (2006.01)

(52) U.S. Cl. ..... Plt./355
(58) Field of Classification Search ..... Plt./355
See application file for complete search history.

*Primary Examiner*—Kent L. Bell
(74) *Attorney, Agent, or Firm*—C. A. Whealy

(57) ABSTRACT

A new and distinct cultivar of *Aster* plant named 'Yopeter the Third', characterized by its uniform, upright and mounded plant habit; freely branching growth habit; dark green-colored foliage; uniform and freely flowering habit; natural flowering season late September in the northern hemisphere; decorative-type inflorescences with light violet-colored ray florets; and good garden performance.

1 Drawing Sheet

Botanical designation: *Aster hybrida.*
Cultivar denomination: 'Yopeter the Third'.
Cross-reference to related applications: *Aster* Plant Named 'Yomarie the Third'; Mark A. Smith, Applicant; U.S. Plant patent application Ser. No. 11/705,876.

BACKGROUND OF THE INVENTION

The present invention relates to a new and distinct cultivar of *Aster* plant, botanically known as *Aster hybrida* and hereinafter referred to by the name 'Yopeter the Third'.

The objective of the breeding program is to create new potted *Aster* cultivars with uniform and rounded plant growth habit, good vigor and strong branching habit, numerous inflorescences, desirable and unique floret colors, and good garden performance.

The new *Aster* originated from an open-pollination in August, 2003, in Salinas, Calif. of the *Aster hybrida* cultivar Pixie Dark, not patented, as the female, or seed, parent with an unknown *Aster hybrida* seedling selection, as the male, or pollen, parent. The new *Aster* was discovered and selected by the Inventor as a single flowering plant within the progeny of the stated open-pollination in a controlled environment Alva, Fla. in October, 2004. The selection of this plant was based on its uniform plant growth habit, vigor and desirable ray floret color.

Asexual reproduction of the new *Aster* by vegetative tip cuttings was first conducted in Alva, Fla. in December, 2004. Asexual reproduction by cuttings has shown that the unique features of this new *Aster* are stable and reproduced true to type in successive generations.

SUMMARY OF THE INVENTION

Plants of the cultivar Yopeter the Third have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yopeter the Third'. These characteristics in combination distinguish 'Yopeter the Third' as a new and distinct potted *Aster* cultivar:

1. Uniform, upright and mounded plant habit.
2. Freely branching growth habit.
3. Dark green-colored foliage.
4. Uniform and freely flowering habit.
5. Natural flowering season late September in the nothern hemisphere.
6. Decorative-type inflorescences with light violet-colored ray florets.
7. Good garden performance.

Plants of the new *Aster* differ from plants of the female parent, the cultivar Pixie Dark, in the following characteristics:

1. Plants of the new *Aster* flower about two weeks later than plants of the cultivar Pixie Dark when grown under natural season conditions.
2. Plants of the new *Aster* and the cultivar Pixie Dark differ in inflorescence form as plants of the cultivar Pixie Dark have daisy-type inflorescences.
3. Plants of the new *Aster* flower more uniformly than plants of the cultivar Pixie Dark.
4. Plants of the new *Aster* have larger inflorescences than plants of the cultivar Pixie Dark.
5. Plants of the new *Aster* and the cultivar Pixie Dark differ in ray floret color.

Plants of the new *Aster* differ primarily from plants of the cultivar Yomarie the Third in ray floret coloration.

Plants of the new *Aster* can be compared to plants of the *Aster* cultivar Milka, disclosed in U.S. Plant Pat. No. 10,624. In side-by-side comparisons conducted in Alva, Fla., plants of the new *Aster* differed from plants of the cultivar Milka in the following characteristics:

1. Plants of the new *Aster* were shorter than plants of the cultivar Milka.

2. Plants of the new *Aster* were fuller and more rounded than plants of the cultivar Milka.

Plants of the new *Aster* can be compared to plants of the *Aster* cultivar Victoria Fanny, disclosed in U.S. Plant Pat. No. 13,360. In side-by-side comparisons conducted in Alva, Fla., plants of the new *Aster* differed from plants of the cultivar Victoria Fanny in the following characteristics:

1. Plants of the new *Aster* were smaller and more mounding than plants of the cultivar Victoria Fanny.
2. Plants of the new *Aster* flowered about a few days later than plants of the cultivar Victoria Fanny when grown under natural season conditions.
3. Plants of the new *Aster* had smaller inflorescences than plants of the cultivar Victoria Fanny.
4. Plants of the new *Aster* and the cultivar Victoria Fanny differed in ray floret coloration.

BRIEF DESCRIPTION OF THE PHOTOGRAPHS

The accompanying photographs illustrate the overall appearance of the new *Aster*. These photographs show the colors as true as it is reasonably possible to obtain in colored reproductions of this type. Colors in the photographs may differ slightly from the color values cited in the detailed botanical description which accurately describe the colors of the new *Aster*.

The photograph at the bottom of the sheet comprises a side perspective view of a typical flowering plant of 'Yopeter the Third'.

The photograph at the top of the sheet is a close-up view of typical inflorescences of 'Yopeter the Third'.

DETAILED BOTANICAL DESCRIPTION

The aforementioned photographs and following observations and measurements describe plants grown during the summer in Pendleton, S.C. in an outdoor nursery and under conditions and practices which approximate those generally used in commercial potted *Aster* production. During the production of the plants, day temperatures averaged 32° C. and night temperatures averaged 21° C. Rooted cuttings were planted in 20 cm-containers, exposed to natural season conditions. Plants used in the photographs and for the description were about three months old. In the following description, color references are made to The Royal Horticultural Society Colour Chart, 1995 Edition, except where general terms of ordinary dictionary significance are used.

Botanical classification: *Aster hybrida* cultivar Yopeter the Third.

Parentage:

*Female, or seed, parent.*—*Aster hybrida* cultivar Pixie Dark, not patented.

*Male, or pollen, parent.*—Unknown *Aster hybrida* seedling selection, not patented.

Propagation:

*Type.*—Terminal vegetative cuttings.

*Time to initiate roots.*—About ten days at temperatures of about 22° C.

*Time to produce a rooted young plant.*—About 16 to 18 days at temperatures of about 22° C.

*Root description.*—Fine, fibrous; white in color.

*Rooting habit.*—Freely branching.

Plant description:

*Appearance.*—Herbaceous decorative-type potted *Aster*. Upright with lateral branches somewhat outwardly spreading; inverted triangle with uniformly mounded crown. Strong and freely branching growth habit with about 12 to 14 primary lateral branches each with numerous secondary and tertiary branches; dense and full plants. Vigorous growth habit.

*Plant height.*—About 29 cm.

*Plant width.*—About 38 cm.

*Lateral branches.*—Length: About 18 cm. Diameter: About 2.5 mm. Internode length: About 1.4 cm. Strength: Strong. Texture: Smooth, glabrous. Color: Close to 147A.

Foliage description:

*Arrangement.*—Alternate, simple; sessile.

*Length.*—About 2.6 cm.

*Width.*—About 4 mm.

*Shape.*—Lanceolate.

*Apex.*—Acute.

*Base.*—Clasping.

*Margin.*—Entire.

*Texture, upper and lower surfaces.*—Smooth, glabrous.

*Color.*—Developing foliage, upper and lower surfaces: Close to 147A. Fully expanded foliage, upper surface: Close to 147A; venation, 147B. Fully expanded foliage, lower surface: Close to 147B; venation, 147B.

Inflorescence description:

*Appearance.*—Decorative-type inflorescence form with ligulate-shaped ray florets. Inflorescences borne on terminals above and beyond the foliage. Disk and ray florets arranged acropetally on a capitulum. Inflorescence not fragrant.

*Flowering response.*—Under natural conditions, plants flower in late September in the Northern Hemisphere. Inflorescences persistent. Inflorescences last about five weeks on the plant.

*Quantity of inflorescences.*—Freely flowering, about 50 inflorescences develop per lateral stem.

*Inflorescence bud.*—Height: About 1.4 cm. Diameter: About 6 mm. Shape: Ovoid. Color: Close to 84C.

*Inflorescence size.*—Diameter: About 2.8 cm. Depth (height): About 1.7 cm. Diameter of disc: About 1 mm; inconspicuous. Receptacle height: About 7 mm. Receptacle diameter: About 1.1 cm.

*Ray florets.*—Length: About 1.4 cm. Width: About 3.5 mm. Shape: Ligulate. Apex: Acute. Base: Acute to attenuate. Margin: Entire. Texture, upper and lower surfaces: Smooth, glabrous, satiny. Orientation: Initially upright, then about 90° from vertical or perpendicular to peduncle; apices reflexing with development. Number of ray florets per inflorescence: About 344 arranged in about 18 whorls. Color: When opening, upper surface: Close to 85A. When opening, lower surface: Close to 85C. Fully opened, upper surface: Close to 85A; color becoming closer to 85D with development. Fully opened, lower surface: Close to 85B; color becoming closer to 85D with development.

*Disc florets.*—Arrangement: Massed at center of receptacle. Shape: Tubular. Apex: Five-pointed. Length: About 2 mm. Width: Less than 1 mm. Number of disc florets per inflorescence: About eight or ten. Color, immature and mature: Close to 155A.

*Phyllaries.*—Number of phyllaries per inflorescence: About 60 arranged in about 14 whorls. Length: About 6 mm. Width: About 1 mm. Shape: Lanceolate. Apex: Acute. Base: Truncate. Texture, upper and lower surfaces: Smooth, glabrous. Color, upper and lower surfaces: Close to 147A.

*Peduncles.*—Length: First peduncle: About 4.7 cm. Fourth peduncle: About 3.2 cm. Diameter (first peduncle): About 1 mm. Angle: Upright to about 30° to 45° from vertical. Strength: Strong, flexible. Texture: Smooth, glabrous; longitudinally ridged. Color: Close to 147A.

*Reproductive organs.*—Androecium: None observed. Gynoecium: Present on both ray and disc florets. Pistil length: About 5 mm. Stigma shape: Bi-parted. Stigma color: Close to 157A. Style length: About 2.5 mm. Style color: Close to 157C. Ovary color: Close to 145C.

*Seed/fruit.*—Seed and fruit production has not been observed.

Disease/pest resistance: Resistance to pathogens and pests common to *Asters* has not been observed on plants grown under commercial conditions.

Garden performance: Plants of the new *Aster* have been observed to be rain and wind tolerant and to tolerate temperatures from 2° C. to about 38° C.

It is claimed:

1. A new and distinct *Aster* plant named 'Yopeter the Third' as illustrated and described.

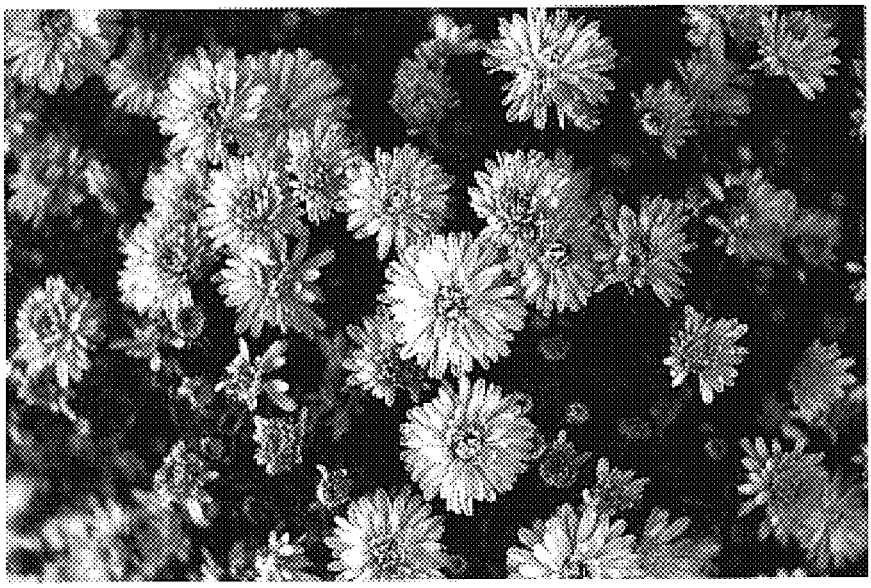
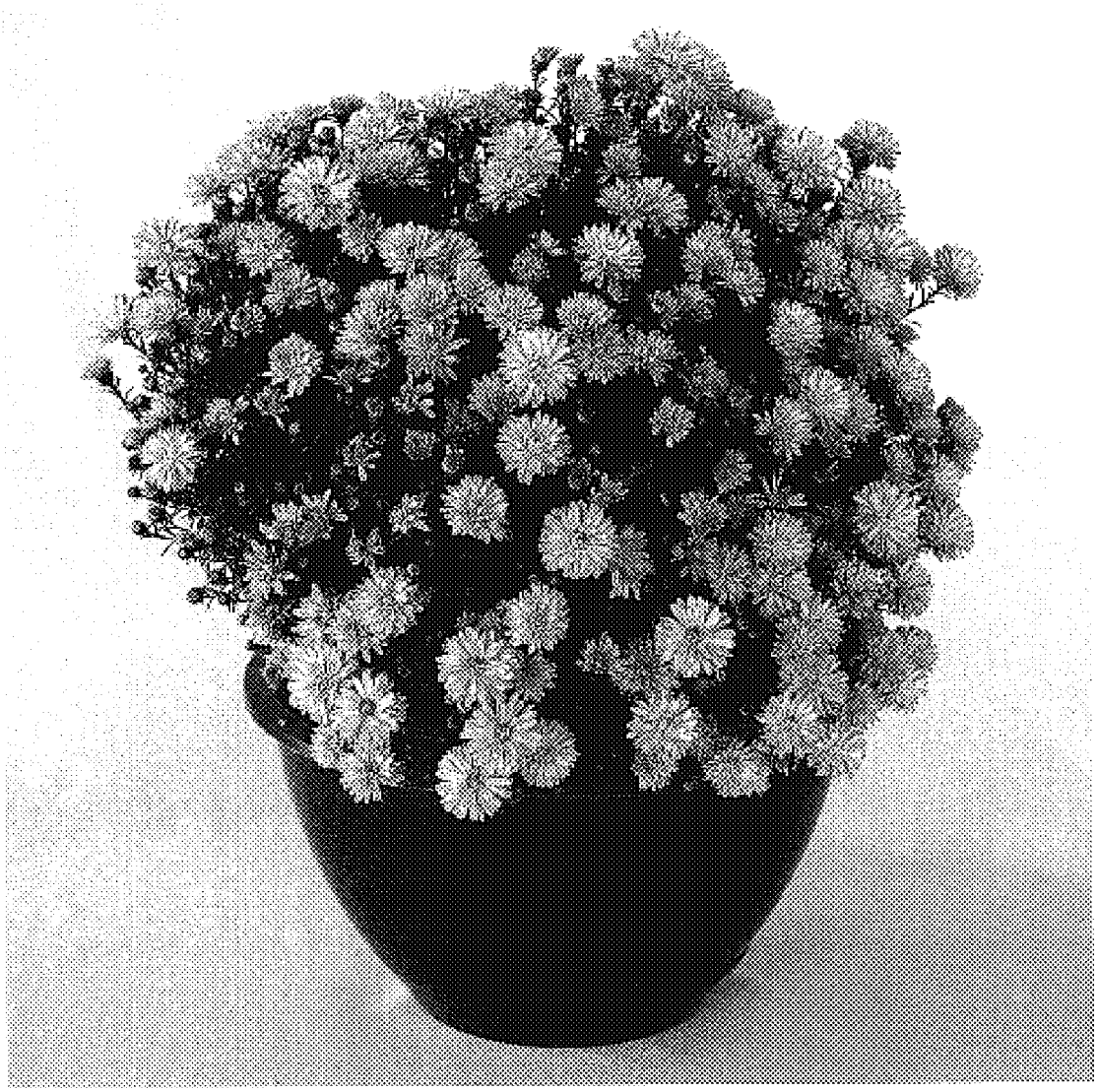

* * * * *